United States Patent

Reiter et al.

[11] Patent Number: 5,118,703
[45] Date of Patent: Jun. 2, 1992

[54] PRODRUGS OF ANTIINFLAMMATORY 3-ACYL-2-OXINDOLE-1-CARBOXAMIDES

[75] Inventors: Lawrence A. Reiter, Mystic; Thomas C. Crawford, Glastonbury, both of Conn.

[73] Assignee: Pfizer Inc., New York, N.Y.

[21] Appl. No.: 675,883

[22] PCT Filed: Oct. 18, 1988

[86] PCT No.: PCT/US88/03658

§ 371 Date: Apr. 8, 1991

§ 102(e) Date: Apr. 8, 1991

[87] PCT Pub. No.: WO90/04393

PCT Pub. Date: May 3, 1990

[51] Int. Cl.$^5$ .............. A61K 31/40; C07D 403/06
[52] U.S. Cl. .................... 514/414; 514/80; 514/418; 548/414; 548/468; 548/486
[58] Field of Search .............. 514/414, 418, 80; 548/486, 468, 414

[56] References Cited

U.S. PATENT DOCUMENTS

| 2,872,372 | 3/1959 | Hull | 167/58 |
| 3,564,009 | 2/1971 | Yamamoto | 568/468 |
| 3,634,453 | 1/1972 | McManus | 514/960 |
| 3,923,996 | 12/1975 | Hardtmann | 424/274 |
| 4,556,672 | 12/1985 | Kadin | 548/127 |
| 4,752,609 | 6/1988 | Kadin | 548/468 |
| 5,036,009 | 7/1991 | Allen et al. | 548/468 |

FOREIGN PATENT DOCUMENTS 0365194 4/1990 European Pat. Off.
0393936 10/1990 European Pat. Off.
0421749 4/1991 European Pat. Off.
8805656 8/1988 PCT Int'l Appl.

OTHER PUBLICATIONS

Capuano, L., et al., "Neue Ringumwandlungen in der Isatinreihe, III", Chem. Ber. 109: 723-739 (1976).
Chemical Abstract No. 136057s, vol. 78, p. 363 (1973).
Chemical Abstract No. 185555r, vol. 110, p. 39 (1989).

Primary Examiner—Joseph Paul Brust
Assistant Examiner—Jacqueline Haley
Attorney, Agent, or Firm—Peter C. Richardson; J. Trevor Lumb; A. Dean Olson

[57] ABSTRACT

Certain enol ethers and esters of the formula

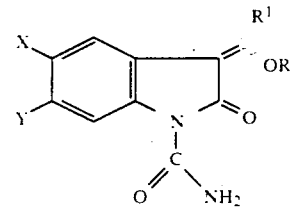

where X and Y are each hydrogen, fluoro or chloro; $R^1$ is 2-thienyl or benzyl and R is alkanoyl, cycloalkylcarbonyl, phenylalkanoyl, chlorobenzoyl, methoxybenzyl, phenyl, thenoyl, omega-alkoxycarbonylalkanoyl, alkoxycarbonyl, phenoxycarbonyl, 1-alkoxyalkyl, 1-alkoxycarbonyloxyalkyl, alkyl, alkylsulfonyl, methylphenylsulfonyl or dialkylphosphonate are useful as prodrug forms the known 3-acyl-2-oxindole-1-carboxamide antiinflammatory and analgesic agents.

33 Claims, No Drawings

PRODRUGS OF ANTIINFLAMMATORY 3-ACYL-2-OXINDOLE-1-CARBOXAMIDES

BACKGROUND OF THE INVENTION

The present invention is concerned with antiinflammatory agents and, in particular, with enol esters and ether prodrugs of 3-acyl-2-oxindole-1-carboxamides, a class of known nonsteroidal antiinflammatory agents.

The use of oxindole as antiinflammatory agents was first reported in U.S. 3,634,453, and consisted of 1-substituted-2-oxindole-3-carboxamides. Recently, a series of 3-acyl-2-oxindole-1-carboxamides was disclosed in U.S. Pat. No. 4,556,672 to be inhibitors of the cyclooxygenase (CO) and lipoxygenase (LO) enzymes and to be useful as analgesic and antiinflammatory agents in mammalian subjects.

SUMMARY OF THE INVENTION

The present invention provides antiinflammatory ether and ester prodrugs of the formula

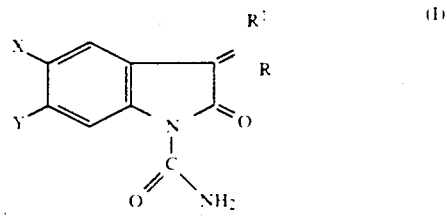

wherein X and Y are each hydrogen, fluoro or chloro; $R^1$ is 2-thienyl or benzyl; and R is alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl said alkoxy having one to three carbon atoms and said alkanoyl having three to five carbon atoms; alkoxy carbonyl of two to ten carbon atoms; phenoxycarbonyl; 1-(acyloxy)alkyl said acyl having one to four carbon atoms and said alkyl having two to four carbon atoms; 1-(alkoxycarbonyloxy)alkyl said alkoxy having two to five carbon atoms and said alkyl having one to four carbon atoms; alkyl of one to three carbon atoms; alkylsulfonyl of one to three carbon atoms; methylphenylsulfonyl or dialkylphosphonate said alkyl each of one to three carbon atoms.

Particularly preferred are compound of formula (I) where $R^1$ is 2-thienyl, X is chloro, Y is hydrogen and R is alkanoyl of two to ten carbon atoms. Preferred within this group are compounds where R is acetyl, propionyl and i-butyryl.

A second preferred group of compounds of formula (I) are those where $R^1$ is 2-thienyl, X is chloro, Y is hydrogen and R is phenylalkanoyl of seven to ten carbon atoms. Especially preferred within this group is the compound where R is phenylacetyl.

A third preferred group of compounds are those of formula (I) where $R^1$ is 2-thienyl, X is chloro, Y is hydrogen and R is omega alkoxycarbonylalkanoyl, said alkoxy having one to three carbon atoms and said alkanoyl having three to five carbon atoms. Especially preferred within this group is the compound where R is omega ethoxycarbonylpropionyl.

A fourth group of preferred compounds of formula (I) are those where $R^1$ is 2-thienyl, X is chloro, Y is hydrogen and R is alkoxycarbonyl of two to ten carbon atoms. Especially preferred within this group are compounds where R is methoxycarbonyl, ethoxycarbonyl and n-hexoxycarbonyl.

A fifth group of preferred compounds of formula (I) are those where $R^1$ is 2-thienyl, X is chloro, Y is hydrogen and R is 1-(alkoxycarbonyloxy)alkyl said alkoxy having two to five carbon atoms and said alkyl having one to four carbon atoms. Especially preferred within this group is the compound where R is 1-(ethoxycarbonyloxy)ethyl.

A sixth group of preferred compounds of formula (I) are those where $R^1$ is 2-thienyl, X is chloro, Y is hydrogen and R is alkylsulfonyl of one to three carbon atoms. Especially preferred within this group is the compound where R is methylsulfonyl.

A seventh group of preferred compounds of formula (I) are those where $R^1$ is 2-thienyl, X is fluoro, Y is chloro and R is alkanoyl of two to ten carbon atoms. Especially preferred within this group are the compounds where R is acetyl, propionyl and i-butyryl.

An eighth group of preferred compounds of formula (I) are those where $R^1$ is 2-thienyl, X is fluoro, Y is chloro and R is alkoxycarbonyl of two to ten carbon atoms. Especially preferred within this group are the compounds where R is methoxycarbonyl, ethoxycarbonyl and n-hexoxycarbonyl.

The ninth group of preferred compounds of formula (I) are those where $R^1$ is benzyl, X is hydrogen, Y is fluoro and R is alkanoyl having two to ten carbon atoms. Especially preferred within this group is the compound where R is acetyl.

The tenth group of preferred compounds of formula (I) are those where $R^1$ is benzyl, X is hydrogen, Y is fluoro and R is alkoxycarbonyl of two to ten carbon atoms. Especially preferred with this group is the compound where R is methoxycarbonyl.

The present invention also comprises a method for treating inflammation in a mammal which comprises administering to said mammal an antiinflammatory effective amount of a compound selected from those of formula (I).

The enol ethers and esters of the present invention are not enolic acids as the parent compounds are and show reduced gastric irritation when compared to said parent compounds.

The term "prodrug" refers to compounds which are drug precursors which, following administration and absorption, release the drug in vivo via some metabolic process.

While all of the usual routes of administration are useful with the invention compounds, the preferred route of administration is oral. After gastrointestinal absorption, the present compounds are hydrolyzed in vivo, to the corresponding compounds of formula (I) where R is hydrogen, or a salt thereof. Since the prodrugs of the invention are not enolic acids, exposure of the gastrointestinal tract to the acidic parent compound is thereby minimized. Further, since gastrointestinal complications have been noted as a major adverse reaction of acid non-steroidal antiinflammatory drugs [see e.g., DelFavero in "Side Effects of Drugs Annual 7", Dukes and Elis, Eds. Excerpta Medica, Amsterdam, 1983, p. 104-115], the invention compounds (I) have a distinct advantage over the parent enolic compounds.

In converting the 3-acyl-2-oxindole-1-carboxamides to the compounds of formula I, the substituents on the exocyclic double bond at the 3-position can be syn, anti or a mixture of both. Thus the compounds of the structures

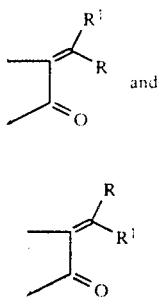

and or mixtures thereof are depicted as

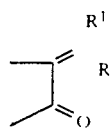

All forms of these isomers are considered part of the present invention.

DETAILED DESCRIPTION OF THE INVENTION

There are two methods employed in the synthesis of the compounds of the present invention; the first method comprises treating a solution of the appropriate 3-acyl-2-oxindole-1-carboxamide and an equimolar amount of triethylamine in a reaction-inert solvent such as chloroform, at 0° C. with an equimolar amount, plus a slight excess of the requisite acid chloride, chloroformate, oxonium salt or alkylating agent. The reaction is allowed to warm to room temperature and remain for about 2-3 hours. If the starting oxindole is not completely reacted the mixture is cooled to 0° C., additional acylating or alkylating agent is added and the process repeated until all the starting oxindole is consumed.

The product is isolated from the reaction solvent after it has been washed with 1N hydrochloric acid followed by a saturated sodium bicarbonate solution extraction. The residual product, remaining after the solvent has been removed in vacuo, is purified by recrystallization or chromatography.

The second procedure, useful in the preparation of the products of the present invention, consists of contacting, in an anhydrous reaction-inert solvent such as acetone, the appropriate 3-acyl-2-oxindole-1-carboxamide a three-fold molar excess of the requisite alpha-chloroalkylcarbonate, a five fold molar excess of sodium iodide and a two fold molar excess of anhydrous potassium carbonate and heating said reaction mixture at reflux for 16 hours.

The reaction mixture is diluted with water and the product extracted with a water-immiscible solvent, such as diethyl ether or chloroform. Concentration of the solvent containing the product provides the crude material, which can be purified by recrystallization and/or chromatography.

The 3-acyl-2-oxindole-1-carboxamides required as starting materials are available by methods well known in the art, see, for example, the reference to these compounds cited above. The other starting reagents noted above are available commercially, or are prepared by well known methods.

The prodrugs of formula (I) are evaluated for their antiinflammatory and analgesic activity according to known methods such as the rat foot edema test, rat adjuvant-induced arthritis test or phenylbenzoquinone-induced writhing test in mice, as previously used in the evaluation of the parent compounds and described in the references cited above and elsewhere in the literature: see e.g., C. A. Winter, in "Progress in Drug Research" edited by E. Jucker, Birkhauser Verlag, Basel, Vol. 10, 1966, pp. 139-192.

In comparison with the parent 3-acyl-2-oxindole-1-carboxamides the novel prodrugs of formula (I) are found to have reduced ability to inhibit prostaglandin synthesis from arachidonic acid in tests carried out by a modification of the method of T. J. Carty et al., *Prostaglandins*, 19, 51-59 (1980). In the modified procedure cultures of rat basophilic leukemic cells (RBL-1), prepared by the method of Jakschik et al., ibid., 16, 733 (1978), are employed in place of mouse fibroblast (MC5-5) and rabbit synovial cell cultures. Thus, the invention compounds themselves are relatively inactive as antiinflammatory agents, but they give rise to an active antiinflammatory compound upon hydrolysis in vivo. Since the compounds (I) are not enolic acids and it is known that the hydrolysis takes place after the prodrug leaves the stomach, they will significantly reduce the gastric irritation caused by oral administration of the parent enolic compounds.

On a molar basis, the present prodrugs are generally dosed at the same level and frequency as the known 3-acyl-2-oxindole-1-carboxamides from which they are derived. However, the non-enolic nature of the present compounds will generally permit higher tolerated oral doses, when such higher dosage is required in the control of pain and inflammation.

The present prodrugs are also formulated in the same manner, and administered by the same routes as the known parent compounds, as described in the above cited reference. The preferred route of administration is oral, thus taking particular advantage of the nonenolic nature of the present compounds.

The present invention is illustrated by the following examples, but is not limited to the specific details of these examples.

EXAMPLE 1

General Procedures

Method A

To a slurry of a 3-acyl-2-oxindole-1-carboxamide in chloroform is added an equimolar amount of triethylamine. The resulting solution is cooled to 0° C. and a slight excess of the appropriate acid chloride, chloroformate, oxonium salt or alkylating agent added. After stirring for 2 hours at 0° C. and then at room temperature for 2 hours, if the 3-acyloxindole-1-carboxamide has not been consumed, then the mixture is again cooled to 0° C. and additional acid chloride chloroformate or oxonium salt is added and the mixture stirred at 0° C. for 2 hours and then at room temperature for 2 hours. This process may be repeated in order to ensure complete consumption of the 3-acyloxindole-1-carboxamide. Upon completion of the reaction, the mixture is filtered and the filtrate washed with 1N hydrochloric acid (2X) and saturated sodium bicarbonate solution (2X). The organic layer is dried with MgSO₄, filtered and concentrated in vacuo. The resulting product is purified by recrystallization or chromatography.

Method B

A mixture of 3-acyl-2-oxindole-1-carboxamide, a 3-fold molar excess of the appropriate alpha-chloroalkyl- or alpha-chloro(aralkyl)carbonate, a 5-fold molar excess of sodium iodide, and a 2-fold molar excess of anhydrous potassium carbonate (dried under high vacuum at 165° C. for 1 hour) in acetone (dried over molecular sieves) is refluxed for 16 hours. The cooled mixture is then diluted with water and extracted with ether. The combined ether extracts are dried with MgSO₄, filtered, and the filtrate concentrated in vacuo. The resulting crude product is purified by chromatography and/or recrystallization.

EXAMPLE 2

Following the indicated procedure, and starting with the requisite reagents the indicated prodrugs were prepared:

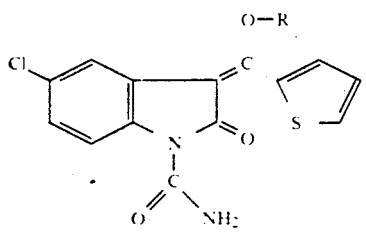

Esters:

(R = —COCH₃)—Method A; yield 53% after recrystallization from 2-propanol; mp 173°-176° C.; mass spectrum m/e (relative intensity) M⁻, 362 (<1.0), 322 (4.2), 320 (11.0), 296 (1.8), 279 (18.2), 277 (44.4), 248 (10.6), 195 (77.7), 193 (100), 185 (12.3), 165 (13.4), 137 (42.8), 111 (88.2), 102 (20.0), 83 (23.9); ¹H-NMR (CDCl₃) delta 2.39, 2.53 (3H, 2s), 5.31 (1H, br s), 7.2-7.35 (2H, m), 7.48, 7.55 (1H, 2d, J=2.1 Hz), 7.6-8.3 (3H, m), 8.54 (1H, br s). Anal. calcd for C₁₆H₁₁ClN₂O₄S (362.79): C, 52.97; H, 3.06; N, 7.72. Found: C, 52.91; H, 2.95; N, 7.97.

(R = —COCH₂CH₃)—Method A; yield 18% after recrystallization from 2-propanol; mp 183°-185° C.; mass spectrum m/e (relative intensity) M⁻, 378, 376 (<1, 1.2), 333 (0.7), 322 (6.4), 320 (18.4), 279 (17.8), 277 (44.3), 250 (2.3), 248 (9.0), 195 (27.0), 193 (100), 137 (7.8), 111 (24.1), 57 (30.0); ¹H-NMR (d₆-Me₂SO) delta 1.0-1.3 (3H, m), 2.7-3.0 (2H, q, J=7.5 Hz), C₁₇H₁₃ClN₂O₄S (376.68): C, 54.18; H, 3.48; N, 7.43. Found: C, 53.86; H, 3.33; N, 7.28.

(R = —CO(CH₂)₅CH₃)—Method A; yield 29% after recrystallization from 2-propanol; mp 189°-190° C.; mass spectrum m/e (relative intensity) M⁻, 432 (0.8), 322 (13.8), 320 (37.5), 279 (34.8), 277 (87.0), 250 (5.0), 248 (17.3), 195 (26.6), 193 (100); ¹H-NMR (CDCl₃) delta 0.95 (3H, m), 1.32-1.55 (6H, m), 1.85 (2H, pentet, J=8 Hz), 2.83 (2H, t, J=8 Hz), 5.35 (1H, br s), 7.25 (1H, m), 7.32 (1H, m), 7.60 (1H, d), 7.72 (1H, m), 8.27 (1H, m), 8.31 (1H, d, J=10 Hz), 8.62 (1H, br s). Anal. calcd for C₂₂H₂₁ClN₂O₄S (432.91): C, 58.26; H, 4.89; N, 6.47. Found: C, 58.18; H, 4.87; N, 6.42.

(R = —CO(CH₂)₈CH₃)—Method A; yield 8% after recrystallization from 2-propanol; mp 120°-122° C.; mass spectrum m/e (relative intensity) M⁻, 431 (<1), 322 (2.9), 320 (8.6), 279 (16.8), 277 (42.6), 262 (0.9), 260 (2.1), 250 (2.4), 248 (9.0), 195 (26.4), 193 (100), 155 (7.4), 137 (6.3), 111 (18.2); ¹H-NMR (d₆-Me₂SO) delta 0.87 (3H, s), 1.30 (13H, br s), 1.50 (1H, m), 1.65 (1H, m), 2.20 (1H, t, J=7.2 Hz), 2.70 (1H, t, J=7.3 Hz), 7.1-8.5 (7H, m). Anal. calcd for C₂₄H₂₇ClN₂O₄S (474.75): C, 60.68; H, 5.73; N, 5.90. Found: C, 60.64; H, 5.76; N, 5.88.

(R = —COCH(CH₃)₂)—Method A; yield 37% after recrystallization from 2-propanol; mp 189°-191° C.; mass spectrum m/e (relative intensity) M⁻, 392, 390 (1.2, 3.5), 322, 320 (11.7, 30.2), 279, 277 (19.2, 48.7), 250, 248 (4.6, 15.5), 195, 193 (28.7, 100); ¹H-NMR (CDCl₃) delta 1.35 (3H, d, J=8 Hz, isomer A), 1.45 (3H, d, J=8 Hz, isomer B), 2.93 (1H, septet, J=8 Hz, isomer A), 3.05 (1H, septet, J=8 Hz, isomer B), 5.38 (1H, br s, isomer A), 5.45 (1H, br s, isomer B), 7.2-7.4 (2H, m), 7.54 (1H, d), 7.7-7.8 (2H, m), 8.2-8.3 (1H, m), 8.48 (1H, br s, isomer B), 8.55 (1H, br s, isomer A) (note: isomer ratio of A to B is approximately 80:20). Exact mass calcd for C₁₈H₁₅ClN₂O₄S: 390.0449. Found: 390.0462.

(R = —COC(CH₃)₃)—Method A; yield 51% after recrystallization from 2-propanol; mp 198°-200° C.; mass spectrum m/e (relative intensity) M⁻, 404 (0.3), 320 (2.4), 277 (22.0), 259 (1.1), 248 (8.3), 193 (66.6), 137 (6.6), 111 (19.1), 102 (2.4), 85 (21.1), 57 (100); ¹H-NMR (CDCl₃) delta 1.39 (9H, s), 5.47 (1H, br s), 7.23 (2H, m), 7.50 (1H, d, J=2.2 Hz), 7.71 (1H, dd, J=1.1, 5.0 Hz), 7.77 (1H, dd, J=1.1, 3.8 Hz), 8.25 (1H, d, J=8.8 Hz), 8.57 (1H, br s). Anal. calcd for C₁₉H₁₇ClN₂O₄S (404.85): C, 56.36; H, 4.23; N, 6.92. Found: C, 56.05; H, 4.23; N, 6.86.

(R = —CO(cyclohexyl))—Method A; yield 10% after recrystallization from 2-propanol; mp 189°-190° C.; mass spectrum m/e (relative intensity) M⁻, 430 (0.7), 381 (<1), 322 (2.3), 320 (6.5), 279 (8.0), 277 (19.8), 195 (16.3), 193 (60.0), 111 (67.1), 83 (100), 55 (25.8); ¹H-NMR (d₆-Me₂SO) delta 1.05-1.70 (11H, set of m), 6.95-7.10 (1H, m), 7.18 (1H, t, J=4.4 Hz), 7.31 (1H, dd, J=2.2, 8.8 Hz), 7.4 (1H, m), 7.70-8.15 (4H, set of m). Anal. calcd for C₂₁H₁₉ClN₂O₄S (429.72): C, 58.53; H, 4.44; N, 6.50. Found: C, 58.34; H, 4.32; N, 6.43.

(R = —COPh)—Method A; yield 44% after recrystallization from acetic acid; mp 228°-230° C.; mass spectrum m/e (relative intensity) M⁻, 424 (3.0), 381 (1.9), 277 (3.9), 260 (6.9), 248 (10.2), 232 (0.9), 212 (2.3), 185 (4.7), 168 (24.1), 140 (6.5), 105 (100), 77 (27.1); ¹H-NMR (CDCl₃) delta 5.55 (1H, br s), 7.30 (3H, m), 7.55 (3H, m), 7.65 (1H, m), 7.74 (1H, dd, J=1.0, 5.0 Hz), 7.84 (1H, dd, J=1.0, 3.8 Hz), 8.2-8.3 (3H, m), 8.45 (1H, br s). Anal. calcd for C₂₁H₁₃ClN₂O₄S.H₂O (442.87): C, 56.95; H, 3.41; N, 6.32. Found: C, 57.24; H, 3.08; N, 6.09.

(R = —COCH₂Ph)—Method A; yield 3% after filtration through silica gel (10:90 - methanol/chloroform) and two recrystallizations from 2-propanol; mp 207°-208° C.; mass spectrum m/e (relative intensity) M⁻, 438 (<1), 395 (<1), 322 (9.6), 320 (26.4), 279 (17.1), 277 (43.1), 195 (14.6), 193 (54.3), 91 (100); ¹H-NMR (CDCl₃/d₆-Me₂SO) delta 3.96 (2H, s), 6.20 (1H, br s), 7.02 (1H, dd, J=4.0, 5.1 Hz), 7.15 (1H, dd, J=2.2, 8.8 Hz), 7.3-7.4 (6H, m), 7.57 (1H, dd, J=1.2, 5.1 Hz), 7.90 (1H, dd, J=1.2, 4.0 Hz), 8.15 (1H, d, J=8.8 Hz), 8.30 (1H, br s). Anal. calcd for C₂₂H₁₅ClN₂O₄S (438.87): C, 60.20; H, 3.45; N, 6.38. Found: C, 60.53; H, 3.38; N, 6.18.

(R = —CO(CH₂)₃Ph)—Method A; yield 13% after recrystallization from 2-propanol; mp 168°-171° C.;

mass spectrum m/e (relative intensity) M+, not observed, 423 (<1), 322 (1.0), 320 (2.9), 279 (10.2), 277 (25.7), 250 (1.5), 248 (5.6), 195 (26.7), 193 (100), 158 (0.7), 147 (72.1), 91 (99.5); 1H-NMR (d6-Me2SO) delta 1.75-2.05 (2H, m), 2.22 (1H, t, J=7.4 Hz), 2.55-3.00 (3H, m), 6.90-7.65 (9H, m), 7.85-8.50 (4H, m). Anal. calcd for C24H19ClN2O4S (466.75): C, 61.73; H, 4.10; N, 5.99. Found: C, 61.74; H, 4.02; N, 5.89.

(R=—CO(3—Cl—Ph))—Method A; yield 26% after recrystallization from 2-propanol/dimethylformamide; mp 210°-218° C.; mass spectrum m/e (relative intensity) M+, 460, 458 (0.5, 0.6), 279 (1.5), 277 (3.9), 250 (0.9), 248 (2.8), 195 (1.3), 193 (4.6), 141 (43.0), 139 (100), 113 (8.8), 111 (32.8); 1H-NMR (CDCl3) delta 5.28 (1H, br s), 7.25 (2H, m), 7.51 (2H, m), 7.62 (1H, m), 7.74 (1H, dd, J=1.1, 5.0 Hz), 7.84 (1H, dd, J=1.1, 3.8 Hz), 8.07 (1H, m), 8.16 (1H, m), 8.27 (1H, d, J=8.8 Hz), 8.41 (1H, br s). Anal. calcd for C21H12Cl2N2O4S (459.29): C, 54.91; H, 2.63; N, 6.10. Found: C, 54.85; H, 2.59; N, 6.04.

(R=—CO(4—MeO—Ph))—Method A; yield 11% after filtration through silica gel (5:95 - methanol/chloroform) and recrystallization from 2-propanol; mp 198°-199° C.; mass spectrum m/e (relative intensity) M+, 454 (0.3), 411 (0.3), 279 (0.3), 277 (0.6), 250 (1.3), 248 (4.2), 195 (1.1), 193 (4.0), 135 (100); 1H-NMR (CDCl3) delta 4.05, 4.10 (3H, 2s), 5.35, 5.46 (1H, 2 br s), 7.15 (2H, m), 7.40 (3H, m) 7.68 (1H, d, J=2.1 Hz), 7.86 (1H, dd, J=1.1, 5.0 Hz), 7.97 (1H, dd, J=1.1, 3.8 Hz), 8.29 (1H, m), 8.41 (1H, m), 8.60, 8.77 (1H, 2 br s). Anal. calcd for C22H15ClN2O5S (454.87): C, 58.09; H, 3.32; N, 6.16. Found: C, 57.99; H, 3.22; N, 6.07.

(R=—CO(2-thienyl))—Method A; yield 16% after being twice flash chromatographed (1st: chloroform; 2nd: 0.5:99.5 - methanol/chloroform); mp 220°-222° C.; mass spectrum m/e (relative intensity) M+, 432, 430 (0.4, 1.1), 389 (0.4), 387 (0.7), 279 (0.6), 277 (1.7), 113 (5.1), 111 (100); 1H-NMR (d6-Me2SO) delta 7.3-7.5 (4H, m), 7.8-8.4 (7H, m). Exact mass calcd for C19H11ClN2O4S2:429.9849. Found: 429.9825.

(R=—COCH2CH2CO2Et)—Method A; yield 72% after recrystallization from 2-propanol; mp 132°-140° C.; mass spectrum m/e (relative intensity) M+, 448 (<1), 405 (<1), 360 (<1), 305 (1.3), 303 (3.7), 279 (2.4), 277 (6.4), 195 (8.9), 193 (32.9), 129 (100), 111 (12.6), 101 (74.3); 1H-NMR (d6-Me2SO) delta 1.15 (3H, m), 2.5 (2H, m), 2.55-3.2 (2H, complex set of m), 4.05 (2H, m), 6.90-7.45 (3H, complex set of m), 7.70 (1H, m), 7.85-8.45 (4H, complex set of m). Anal. calcd for C20H17ClN2O6 (448.87): C, 53.51; H, 3.82; N, 6.24. Found: C, 53.49; H, 3.70; N, 6.23.

Carbonates (R=—COOCH3)—Method A; yield 29% after recrystallization from 2-propanol/chloroform; mp 180° C. softens, melts 200° C.; mass spectrum m/e (relative intensity) M+, 380, 378 (8.5, 23.8), 337 (7.2), 335 (21.2), 293 (17.3), 291 (39.8), 250 (28.3), 248 (100), 195 (24.9), 193 (86.2), 111 (88.6); 1H-NMR (d6-Me2SO) delta 3.90, 3.95 (3H, 2s), 7.3-7.5 (3H, m), 7.95-8.05 (2H, m), 8.15-8.25 (3H, m). Anal. calcd for C16H11ClN2O5S (378.22): C, 50.73; H, 2.93; N, 7.39. Found: C, 50.84; H, 2.93; N, 7.34.

(R=—COOCH2CH3)—Method A; yield 24% after recrystallization from 2-propanol; mp 170°-175° C.; mass spectrum m/e (relative intensity) M+, 392 (<1.0), 320 (1.2), 305 (3.9), 277 (22.5), 259 (2.6), 248 (17.0), 193 (100), 185 (7.2), 165 (4.0), 111 (18.8); 1H-NMR (CDCl3) delta 1.42 (3H, t, J=7.1 Hz), 4.39 (2H, q, J=7.1 Hz), 5.41 (1H, br s), 7.25 (2H, m), 7.48, 7.66 (1H, 2d, J=2.1 and 2.2 Hz) 7.75 (1H, m), 8.25 (2H, m), 8.57 (1H, br s). Anal. calcd for C17H13ClN2O5S (392.79): C, 51.98; H, 3.34; N, 7.13. Found: C, 51.90; H, 3.26; N, 6.93.

(R=—COOCH(CH3)2)—Method A; yield 37% after recrystallization from 2-propanol; mp 185°-186° C.; mass spectrum m/e (relative intensity) M+, 322, 320 (1.8, 6.5), 303 (1.6), 279 (15.2), 277 (41.3), 250 (2.2), 248 (8.5), 193 (100), 167 (1.7), 165 (2.6), 139 (1.3), 137 (4.3), 111 (12.4), 102 (8.0); 1H-NMR (d6-Me2SO) delta 1.34, 1.37 (6H, 2s), 5.00 (1H, heptet, J=6.2 Hz), 7.35 (1H, t, J=4.3 Hz), 7.50 (1H, dd, J=8.7 Hz), 7.55 (1H, m), 7.96, 8.05 (2H, 2 br s), 8.17 (2H, m), 8.25 (1H, m). Anal. calcd for C18H15ClN2O5S (406.69): C, 53.14; H, 3.72; N, 6.89. Found: C, 52.93; H, 3.65; N, 6.82.

(R=—COO(CH2)5CH3)—Method A; yield 39% after recrystallization from 2-propanol; mp 110°-144° C.; mass spectrum m/e (relative intensity) M+, 448 (0.3), 405 (<1), 322 (1.7), 320 (4.5), 279 (15.9), 277 (39.9), 195 (29.8), 193 (100), 111 (14.8); 1H-NMR (d6-Me2SO) delta 0.85 (3H, br t, J=6.6 Hz), 1.3 (6H, m), 1.6 (2H, m), 4.35 (2H, t, J=6.2 Hz), 7.35 (1H, t, J=4.3), 7.4-7.55 (2H, m), 7.95-8.05 (2H, m), 8.15-8.25 (3H, m). Anal. calcd for C21H21ClN2O5S (448.91): C, 56.18; H, 4.72; N, 6.24. Found: C, 56.11; H, 4.60; N, 6.16.

(R=—COO(CH2)8CH3)—Method A; yield 21% after recrystallization from 2-propanol; mp 118°-120° C.; mass spectrum m/e (relative intensity) M+, 490 (0.6), 368 (0.5), 322 (4.9), 320 (2.2), 279 (32.6), 277 (79.3), 250 (4.9), 248 (16.1), 195 (28.5), 193 (100); 1H-NMR (CDCl3) delta 0.89 (3H, m), 1.2-1.5 (12H, m), 1.76 (2H, m), 4.34 (2H, t, J=6.6 Hz), 5.33 (1H, br s), 7.24 (1H, m), 7.32 (1H, dd, J=2.2, 8.8 Hz), 7.68 (1H, d, J=2.1 Hz), 7.74 (1H, dd, J=1.2, 5.1 Hz), 8.20 (1H, dd, J=1.2, 4.0 Hz), 8.29 (1H, d, J=8.8 Hz), 8.58 (1H, br s). Anal. calcd for C24H22ClN2O5S (490.99): C, 58.71; H, 5.54; N, 5.71. Found: C, 58.87; H, 5.48; N, 5.64.

(R=—COOPh)—Method A; yield 8% after recrystallization from 2-propanol; mp 212°-214° C.; mass spectrum m/e (relative intensity) M+, 442, 440 (1.7, 5.7), 399 (4.4), 397 (9.7), 355 (<1), 354 (<1), 353 (2.9), 352 (1.7), 338 (<1), 336 (2.5), 250 (13.4), 248 (44.3), 234 (9.7), 232 (24.0), 195 (8.1), 193 (27.7), 111 (100); 1H-NMR (CDCl3) delta 5.90 (1H, br s), 7.1-7.4 (7H, m), 7.74 (2H, m), 8.22 (2H, m), 8.39 (1H, br s). Anal. calcd for C21H13ClN2O5S (440.84): C, 57.21; H, 2.97; N, 6.36. Found: C, 56.99; H, 2.98; N, 6.38.

Acetal-esters (R=—CH(CH3)OCOCH3)—Method A with the exceptions that silver nitrate (1 molar equivalent was also included in the reaction mixture and that the reaction mixture was refluxed for 24 hours; yield 9% after twice being flash chromatographed (first: 1:99 -methanol/chloroform, second: 0.5:99.5 - methanol/chloroform) and recrystallization from cyclohexane/ethyl acetate; mp 175°-180° C.; mass spectrum m/e (relative intensity) M+, 408, 406 (<1, <1), 364 (2.9), 362 (1.2), 322 (12.1), 320 (40.2), 279 (25.8), 277 (62.6), 195 (43.3), 193 (100); 1H-NMR (CDCl3) delta 1.70 (3H, d, J=5.4 Hz), 1.94 (3H, s), 5.16 (1H, br, s), 6.31 (1H, q, J=5.4 Hz), 7.23 (1H, dd, J=3.9, 5.2 Hz), 7.27 (1H, d, J=2.2 Hz), 7.52 (1H, dd, 1.2, 3.7 Hz), 7.69 (1H, dd, J=1.1, 5.1 Hz), 7.98 (1H, d, J=2.2 Hz), 8.21 (1H, d, J=8.8 Hz), 8.47 (1H, br s). Anal. calcd for C18H15ClN2O5S (406.83): C, 53.14; H, 3.72; N, 6.89. Found: C, 53.40; H, 3.61; N, 6.85.

Acetal-carbonates (R=—CH(CH₃)OCOOCH₂CH₃)—Method B: yield 32% after flash chromatography (25:75 - ethyl acetate/hexane) and recrystallization from 2-propanol; mp 159°-162° C.; mass spectrum m/e (relative intensity) M⁻, 438, 436 (<1.0, 1.0), 393 (<1.0), 322 (1.9), 320 (5.3), 307 (2.0), 305 (6.3), 279 (9.9), 277 (26.9), 195 (42.5), 193 (100); ¹H-NMR (CDCl₃) delta 1.21 (3H, t, J=7.1 Hz), 1.73 (3H, d, J=5.3 Hz), 4.10 (2H, q, J=5.3 Hz), 5.19 (1H, br s), 7.26 (2H, m), 7.52 (1H, dd, J=1.1, 3.7 Hz), 7.71 (1H, dd, J=1.1, 5.0 Hz), 7.97 (1H, d, J=2.2 Hz), 8.22 (1H, d, J=8.7 Hz), 8.47 (1H, br s). Anal. calcd for C₁₉H₁₇ClN₂O₆S (436.86): C, 52.23; H, 3.92; N, 6.41. Found: C, 52.57; H, 4.44; N, 6.03.

(R=—CH(CH₃)OCOOC(CH₃)₃)—Method B: yield 25% after flash chromatography (25:75 - ethyl acetate/hexane) and recrystallization from 2-propanol; mp 184°-187° C.; mass spectrum m/e (relative intensity) M⁻, 347 (0.8), 322 (4.1), 320 (2.0), 279 (16.2), 277 (53.8), 196 (11.3), 195 (34.5), 194 (13.3), 193 (100); ¹H-NMR (CDCl₃) delta 1.33 (9H, s), 1.71 (2H, d, J=5.4 Hz), 5.21 (1H, br s), 6.14 (1H, q, J=5.2 Hz), 7.26 (2H, m), 7.54 (1H, dd, J=1.2, 3.7 Hz), 7.70 (1H, dd, J=1.2, 5.0 Hz), 8.00 (1H, d, J=2.2 Hz), 8.21 (1H, d, J=8.7 Hz), 8.49 (1H, br s). Anal. calcd. for C₂₁H₂₁ClN₂O₆S (464.91): C, 54.25; H, 4.55; N, 6.03. Found, 54.38; H, 4.58; N, 6.09.

(R=—CH(CH₃)OCOOCH₂Ph)—Method B: yield 11% after flash chromatography (25:75 - ethyl acetate/hexane) and recrystallization from ethyl acetate/hexane; mp 140°-145° C., softens 130° C.; mass spectrum m/e (relative intensity) M⁻, 498 (<1.0), 455 (<1.0), 410 (<1.0), 195 (10.3), 193 (32.2), 111 (62.9), 91 (100); ¹H-NMR (CDCl₃) delta 1.72 (3H, d, J=5 Hz), 5.00 (1H, d, J=11 Hz), 5.04 (1H, d, J=11 Hz), 5.28 (1H, br s), 6.20 (1H, q, J=5 Hz), 7.1-7.3 (7H, m), 7.44 (1H, m), 7.61 (1H, m), 7.93 (1H, d, J=2 Hz), 8.20 (1H, d, J=9 Hz), 8.40 (1H, br s). Anal. calcd for C₂₄H₁₉ClN₂O₆S (498.92): C, 57.77; H, 3.84; N, 5.62. Found: C, 57.78; H, 3.80; N, 5.59.

Ethers (R=—CH₃)—Method A using trimethyloxonium tetrafluoroborate; yield 27% after recrystallization from 2-propanol; mp 186°-188° C.; mass spectrum m/e (relative intensity) M⁻, 335 (2.0), 334 (4.7), 291 (29.7), 277 (18.0), 260 (21.7), 248 (12.6), 193 (100), 185 (14.5), 157 (8.7), 111 (52.5); ¹H-NMR (CDCl₃) delta 3.88 (3H, s), 5.25 (1H, br s), 7.27 (3H, m), 7.69 (1H, d, J=5.7 Hz), 7.88 (1H, d, J=2.2 Hz), 8.21 (1H, d, J=8.7 Hz), 8.49 (1H, br s). Anal. calcd for C₁₅H₁₁ClN₂O₃S (334.76): C, 53.81; H, 3.31; N, 8.37. Found: C, 54.15; H, 3.48; N, 8.10.

(R=CH₂CH₃)—Method A using triethyloxonium tetrafluoroborate; yield 22% after recrystallization from 2-propanol; mp 202°-205° C.; mass spectrum m/e (relative intensity) M⁺, 350, 348 (1.5, 4.6), 320 (<1), 307 (7.3), 305 (19.6), 250 (2.2), 248 (7.4), 195 (27.0), 193 (100), 187 (1.2), 185 (4.7), 167 (1.3), 165 (3.2), 139 (2.8), 137 (8.1), 111 (24.0); ¹H-NMR (d₆-Me₂SO) delta 1.40 (3H, t, J=7.0 Hz), 4.15 (2H, q, J=7.0 Hz), 7.30 (1H, m), 7.35 (1H, dd, J=2.3, 8.7), 7.50 (1H, m), 7.65 (1H, s), 7.90 (1H, d, J=2.3 Hz), 8.00 (1H, dd, J=1.0, 5.0 Hz), 8.05 (1H, s), 8.15 (1H, d, J=8.7 Hz). Anal. calcd for C₁₆H₁₃ClN₂O₃S (348.67): C, 55.09; H, 3.76; N, 8.03. Found:, 54.87; H, 3.62; N, 7.79.

Sulfonates (R=—SO₂CH₃)—Method A: yield 4% after being twice filtered through silica gel (5:95 - methanol/chloroform) and recrystallization from 2-propanol; mp 80°-182° C.; mass spectrum m/e (relative intensity) M⁻, 400, 398 (2.8, 5.6), 357 (6.8), 355 (2.6), 261 (15.3), 259 (45.3), 250 (31.0), 248 (100), 141 (15.4), 139 (42.9), 113 (6.1), 111 (37.7); ¹H-NMR (CDCl₃) delta 3.02 (3H, s), 5.23 (1H, br s), 7.23 (1H, m), 7.37 (1H, dd, J=2.2, 8.8 Hz), 7.76 (2H, m), 8.16 (1H, d, J=2.1 Hz), 8.26 (1H, d, J=8.8 Hz), 8.33 (1H, br s). Anal. calcd for C₁₅H₁₁ClN₂O₅S (398.83): C, 45.17; H, 2.78; N, 7.03. Found: C, 45.30; H, 2.60; N, 6.78.

(R=—SO₂(4—Me—Ph))—Method A: yield 6% after recrystallization from 2-propanol; mp 200°-202° C.; mass spectrum m/e (relative intensity) M⁻, 474 (<1), 433 (1.6), 431 (4.0), 404 (1.6), 402 (3.3), 250 (32.0), 248 (100), 195 (4.4), 193 (15.8), 155 (27.7), 111 (47.8), 91 (42.2); ¹H-NMR (d₆-Me₂SO) delta 2.40 (3H, s), 7.05 (1H, t, J=4.5 Hz), 7.35-7.50 (4H, m), 7.65 (3H, m), 7.90 (3H, m), 8.12 (1H, d, J=8.7 Hz). Anal. calcd for C₂₁H₁₅ClN₂O₅S₂ (474.78): C, 53.10; H, 3.18; N, 5.89. Found: C, 53.09; H, 3.22; N, 5.66.

Phosphonates (R=—PO(OCH₂CH₃)₂)—Method A: yield 14% after being filtered through silica gel (5:95 - methanol/chloroform) and recrystallization from cyclohexane/ethyl acetate; mp 180°-183° C.; mass spectrum m/e (relative intensity) M⁻, 458, 456 (1.2, 3.8), 415 (7.4), 413 (17.4), 261 (31.7), 259 (100), 250 (3.1), 248 (9.2), 196 (17.1), 195 (12.5), 193 (44.6); ¹H-NMR (CDCl₃) delta 1.33 (6H, dt, J=1.2, 7.1 Hz), 4.14 (4H, m), 5.23 (1H, br s), 7.32 (1H, dd, J=2.2, 8.8 Hz), 7.70 (1H, dd, J=1.2, 5.0 Hz), 7.83 (1H, dd, J=1.2, 3.8 Hz), 8.06 (1H, d, J=2.2 Hz), 8.25 (1H, d, J=8.8 Hz), 8.46 (1H, br s). Anal. calcd for C₁₈H₁₈ClN₂O₆PS (456.83): C, 47.32; H, 3.97; N, 6.13. Found: C, 47.25; H, 3.83; N, 6.08.

EXAMPLE 2

Starting with the appropriate reagents and using the indicated procedure the following compounds were prepared:

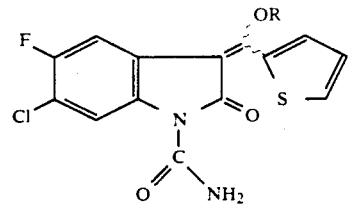

Esters (R=—COCH₃)—Method A; yield 16% after recrystallization from 2-propanol; mp 190°-203° C.; mass spectrum m/e (relative intensity) M⁺, 382, 380 (1.6, 7.7), 340 (36.8), 338 (98.1), 297 (16.5), 295 (43.4), (<1), 277 (2.1), 268 (3.4), 266 (8.3), 256 (1.4), (5.2), 213 (38.6), 211 (100), 111 (26.7); ¹H-NMR (d₆-Me₂SO) delta 1.9, 2.4 (3H, 2s), 7.09-7.40 (2H, set m), 7.55-7.80 (1H, set of m), 7.95-8.50 (4H, set of m). Anal. calcd for C₁₆H₁₀ClFN₂O₄S (380.66): C, 50.47; H, 2.65; N, 7.36. Found: C, 50.13; H, 2.52; N, 7.19.

(R=—COCH₂CH₃)—Method A; yield 10% after filtration through silica gel (5:95 - methanol/chloroform) and recrystallization from 2-propanol; mp 182°–188° C.; mass spectrum m/e (relative intensity) M⁻, 396, 394 (<1, 1.3), 340 (7.2), 338 (16.2), 297 (12.1), 295 (32.5), 268 (2.7), 266 (7.1), 213 (26.1), 211 (100), 111 (40.8), 57 (94.2); ¹H-NMR (d₆-Me₂SO) delta 1.18 (3H$_{a,b}$, m) 2.22 (2H$_a$, q, J=7.5 Hz), 2.71 (2H$_b$, q, J=7.5 Hz), 7.09–7.70 (2H$_{a,b}$, m), 7.95–8.48 (5H$_{a,b}$, m). Anal. calcd for C₁₇H₁₂ClFN₂O₄S (394.80): C, 51.71; H, 3.06; N, 7.10. Found, 51.67; H, 3.01; N, 6.97.

(R=—COCH(CH₃)₂)—Method A; yield 11% after filtration through silica gel and recrystallization from 2-propanol; mp 204°–206° C.; mass spectrum m/e (relative intensity) M⁻, 410, 408 (1.1, 4.1), 340 (11.5), 338 (27.2), 297 (13.2), 295 (33.6), 268 (5.6), 266 (15.0), 213 (25.8), 211 (100), 111 (36.4); ¹H-NMR (d₆-Me₂SO) delta 1.34 (6H, d, J=7.0 Hz), 3.25 (1H, heptet, J=7.0 Hz), 7.33 (1H, dd, J=4.0, 5.1 Hz), 7.48 (1H, d, J=9.6 Hz), 8.00 (1H, br s), 8.03 (1H, br s), 8.13 (1H, dd, J=1.2, 5.0 Hz). Anal. calcd for C₁₈H₁₄ClFN₂O₄S (408.83): C, 52.88; H, 3.45; N, 6.85. Found: C, 52.48; H, 3.32; N, 6.86.

(R=—COCH₂Ph)—Method A; yield 22% after recrystallization from 2-propanol; mp 189°–199° C.; mass spectrum m/e (relative intensity) M⁻, not observed, 340 (18.9), 338 (42.1), 297 (20.7), 295 (54.4), 268 (5.8), 266 (19.6), 213 (17.9), 211 (53.7), 91 (100); ¹H-NMR (d₆-Me₂SO) delta 3.98 (2H$_a$, s), 4.02 (2H$_b$, s), 5.35 (1H, br s), 6.99–7.45 (7H, m), 7.68, 8.00 (2H, 2m), 8.42 (1H, dd, J=5.1, 6.9 Hz), 8.50 (1H, br s). Anal. calcd for C₂₂H₁₄ClFN₂O₄S (456.86): C, 57.83; H, 3.09; N, 6.13. Found: C, 57.53; H, 2.98; N, 6.15.

(R=—COCH₂CH₂COOEt)—Method A; yield 26% after recrystallization from 2-propanol; mp 153°–155° C.; mass spectrum m/e (relative intensity) M⁻, not observed, 321 (3.1), 295 (3.1), 266 (4.5), 213 (8.8), 211 (23.4), 155 (5.2), 129 (100), 111 (12.4), 101 (75.0), 91 (2.7); ¹H-NMR (d₆-Me₂SO) delta 1.12 (3H, 2t, J=7.1 Hz), 2.5–3.5 (4H, complex set of m), 4.05 (2H, 2q, J=7.3 Hz), 7.15–7.40 (2H, complex set of m), 7.70 (1H, m), 7.95–8.43 (4H, complex set of m). Anal. calcd for C₂₀H₁₆ClFN₂O₆S (466.70): C, 51.45; H, 3.45; N, 6.00. Found: C, 51.28; H, 3.26; N, 5.99.

Carbonates (R=—COOCH₃)—Method A; yield 25% after recrystallization from 2-propanol; mp 203°–205° C.; mass spectrum m/e (relative intensity) M⁻, 398, 396 (7.5, 24.5), 355 (4.5), 353 (10.6), 311 (23.8), 309 (49.1), 280 (26.3), 278 (27.9), 268 (30.5), 266 (100), 252 (3.5), 250 (6.9), 240 (3.4), 238 (7.2), 213 (25.2), 211 (56.9), 203 (29.4), 197 (5.6), 182 (6.8), 169 (6.1), 157 (4.5), 155 (12.4), 142 (2.1), 111 (45.4), 97 (5.3), 83 (5.5); ¹H-NMR (d₆-Me₂SO) delta 3.89, 3.95 (3H, 2s), 7.38 (2H, m), 8.00 (3H, m), 8.19 (1H, m), 8.29 (1H, t, J=6.7 Hz). Anal. calcd for C₁₆H₁₀ClFN₂O₅S (396.71): C, 48.43; H, 2.54; N, 7.06. Found: C, 48.41; H, 2.47; N, 6.95.

(R=—COOCH₂CH₃)—Method A; yield 57% after recrystallization from 2-propanol; mp 164°–166° C.; mass spectrum m/e (relative intensity) M⁻, 410 (1.4), 325 (1.8), 323 (5.8), 297 (8.0), 295 (20.5), 268 (6.1), 266 (13.7), 213 (37.6), 211 (100), 203 (7.9), 155 (7.5), 111 (21.0); ¹H-NMR (d₆-Me₂SO) delta 1.30 (3H, t, J=7.1 Hz), 4.32 (2H, q, J=7.1 Hz), 7.35 (2H, m), 8.0 (3H, m), 8.20–8.35 (2H, m). Anal. calcd for C₁₇H₁₂ClFN₂O₅S (410.67): C, 49.70; H, 2.94; N, 6.82. Found: C, 49.76; H, 2.85; N, 6.77.

(R=—COO(CH₂)₅CH₃)—Method A; yield 85% after recrystallization from 2-propanol; mp 128°–135° C.; mass spectrum m/e (relative intensity) M⁻, 468, 466 (0.3, 0.7), 425 (0.3), 424 (0.3), 423 (1.1), 340 (7.0), 338 (14.1), 297 (28.5), 295 (74.5), 213 (34.3), 211 (100); ¹H-NMR (CDCl₃) delta 0.85–0.92 (3H, m), 1.22–1.48 (6H, m), 1.72 (2H, pentet, J=9 Hz), 4.31 (2H$_{a,b}$, t), 5.40 (1H$_{a,b}$, br s), 7.21 (1H$_{a,b}$, m), 7.30 (1H$_a$, d, J=9 Hz), 7.47 (1H$_{b,d}$, J=9 Hz), 7.77 (2H$_a$, 1H$_b$, m), 8.19 (1H$_b$, m), 8.42 (1H$_a$, d J=8 Hz), 8.46 (1H$_b$, d, J=8 Hz), 8.49 (1H$_a$, br s), 8.52 (1H$_b$, br s). Anal. calcd for C₂₁H₂₀ClFN₂O₅S (466.91): C, 54.02; H, 4.32; N, 6.00. Found: C, 53.93; H, 4.26; N, 6.02.

Sulfonates (R=—SO₂CH₃)—Method A; yield 9% after filtration through silica gel and recrystallization from cyclohexane/ethyl acetate; mp 180°–185° C.; mass spectrum m/e (relative intensity) M⁻, 418, 416 (3.4, 7.2), 375 (8.4), 373 (21.8), 296 (6.8), 294 (6.8), 294 (16.0), 279 (7.0), 277 (18.5), 268 (42.7), 266 (100), 111 (65.4). Anal. calcd for C₁₅H₁₀ClFN₂O₅S (416.85): C, 43.22; H, 2.42; N, 6.72. Found: C, 43.37; H, 2.30; N, 6.72.

EXAMPLE 3

Using the indicated procedure and starting with the requisite reagents, the following compounds were prepared:

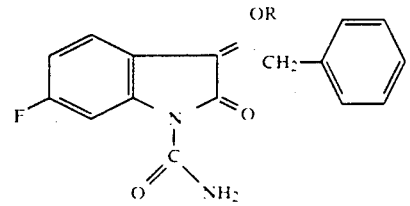

Esters (R=—COCH₃)—Method A; yield 56% after recrystallization from 2-propanol; mp 195°–197° C.; mass spectrum m/e (relative intensity) M⁻, 354 (<1), 312 (32.5), 269 (38.6), 251 (4.8), 221 (12.2), 194 (1.6), 178 (100), 121 (11.1), 91 (23.9), 65 (5.9); ¹H-NMR (d₆-Me₂SO) delta 2.31 (3H s), 7.02 (1H, dt, J=2.6, 8.9 Hz), 7.33 (6H, s), 7.63 (1H, dd, J=5.8, 8.6 Hz), 7.95 (2H, m). Anal. calcd for C₁₉H₁₅FN₂O₄ (354.19): C, 64.40; H, 4.27; N, 7.91. Found: C, 64.30; H, 4.21; N, 7.89.

(R=—COCH₂CH₃)—Method A; yield 23% after recrystallization from 2-propanol; mp 196°–198° C.; mass spectrum m/e (relative intensity) M⁻, 368 (2), 325 (5), 312 (25), 269 (70), 251 (7), 240 (4), 221 (5), 178 (100), 150 (8), 121 (10), 91 (37), 65 (12), 57 (83); ¹H-NMR (d₆-Me₂SO) delta 1.02 (3H, t, J=7.4 Hz), 2.61 (2H, q, J=7.4 Hz), 4.53 (2H, s), 7.02 (1H, dt, J=2.6, 9.2 Hz), 7.32 (6H, m), 7.61 (1H, dd, J=5.8, 8.6 Hz), 7.95 (2H, m). Anal. calcd for C₂₀H₁₇FN₂O₄ (368.20): C, 65.21; H, 4.65; N, 7.61. Found: C, 64.98; H, 4.44; N, 7.54.

(R=—COCH(CH₃)₂)—Method A; yield 28% after recrystallization from 2-propanol; mp 182°–184° C.; mass spectrum m/e (relative intensity) M⁻, 382 (3.5), 339 (<1), 312 (18.6), 269 (18.1), 178 (46.2), 177 (17.4), 91 (31.8), 71 (100); ¹H-NMR (d₆-Me₂SO) delta 1.09 (3H, d, J=7.0 Hz), 2.64 (1H, dq, J=7.0 Hz), 4.65 (2H, s), 5.36 (1H, br s), 6.83 (1H, dt, J=2.5, 8.7 Hz), 7.18–7.33 (5H, m), 7.50 (1H, dd, J=5.6, 8.6 Hz), 8.10 (1H, dd, J=2.5, 10.3 Hz), 8.59 (1H, br s). Anal. calcd for C₂₁H₁₉FN₂O₄ (382.38): C, 65.96; H, 5.01; N, 7.33. Found: C, 65.76; H, 4.94; N, 7.33.

(R=—COPh)—Method A: yield 68% after recrystallization from 2-propanol; mp 188°-190° C.; mass spectrum m/e (relative intensity) M⁻, 416 (2.7), 373 (3.0), 242 (6.1), 177 (6.4), 121 (5.2), 105 (100), 77 (17.8); ¹H-NMR (CDCl₃) delta 4.71 (2H, d), 5.41 (1H, br s), 6.71 (1H, dt, J=2.5, 8.7 Hz), 7.26 (5H, m), 7.42 (1H, dd, J=5.6, 8.6), 7.52 (2H, m), 7.66 (1H, m), 8.03 (2H, d), 8.10 (1H, dd, J=2.5, 10.3 Hz), 8.63 (1H, br s). Anal. calcd for C₂₄H₁₇FN₂O₄·H₂O (434.41): C, 66.35; H, 4.40; N, 6.44. Found: C, 66.14; H, 3.92; N, 6.41.

(R=—COCH₂Ph)—Method A: yield 27% after recrystallization from 2-propanol; mp 201°-202° C.; mass spectrum m/e (relative intensity) M⁻, 430 (0.9), 387 (0.6), 312 (87.5), 269 (100), 178 (64.7), 91 (65.6); ¹H-NMR (d₆-Me₂SO) delta 3.99 (2H, s), 4.48 (2H, s), 6.85 (2H, dt, J=2.6, 8.9 Hz), 7.28 (10H, m), 7.91 (1H, dd, J=2.5, 10.7 Hz), 7.97 (1H, br s), 8.07 (1H, br s). Anal. calcd for C₂₅H₁₉FN₂O₄ (430.25): C, 69.76; H, 4.45; N, 6.51. Found: C, 69.35; H, 4.38; N, 6.62.

(R=—COCH₂CH₂COOEt)—Method A: yield 46% after recrystallization from 2-propanol; mp 159°-161° C.; mass spectrum m/e (relative intensity) M⁻, not observed, 395 (0.4), 352 (0.8), 331 (0.3), 289 (0.6), 269 (6.4), 252 (9.4), 234 (1.9), 222 (6.8), 212 (1.5), 196 (1.1), 178 (24.8), 177 (10.6), 168 (1.5), 130 (7.7), 129 (100), 121 (5.3), 101 (65.8), 91 (10.0); ¹H-NMR (d₆-Me₂SO) delta 1.15 (3H, t, J=7.1 Hz), 2.61 (2H, t, J=6.0 Hz), 2.88 (2H, t, J=6.0 Hz), 4.06 (2H, q, J=7.1 Hz), 4.46 (2H, s), 6.98 (1H, dt, J=2.6, 8.9 Hz), 7.32 (5H, m), 7.67 (1H, dd, J=5.8, 8.6 Hz), 7.93 (1H, dd, J=2.5, 10.7 Hz), 7.98 (1H, br s), 8.08 (1H, br s). Anal. calcd for C₂₃H₂₁FN₂O₆ (440.23): C, 62.72; H, 4.81; N, 6.36. Found: C, 62.75; H, 4.79; N, 6.29.

Carbonates (R=—COOCH₃)—Method A: yield 45% after recrystallization from 2-propanol; mp 178°-180° C.; mass spectrum m/e (relative intensity) M⁻, 370 (16.7), 327 (3.7), 294 (24.0), 251 (100), 235 (11.7), 222 (32.9), 205 (0.4), 204 (3.8), 192 (29.8), 178 (42.5), 164 (2.2), 149 (5.8); ¹H-NMR (d₆-Me₂SO) delta 3.86 (3H, s), 4.58 (2H, s), 7.08 (1H, dt, J=2.6, 9.1 Hz), 7.32 (5H, s), 7.55 (1H, dd, J=5.9, 8.7 Hz), 7.95 (1H, dd, J=2.5, 10.6 Hz), 7.99 (1H, br s), 8.07 (1H, br s). Anal. calcd for C₁₉H₁₅FN₂O₅ (370.19): C, 61.62; H, 4.08; N, 7.56. Found: C, 61.64; H, 4.07; N, 7.55.

(R=—COOCH₂CH₃)—Method A: yield 52% after recrystallization from 2-propanol; mp 189°-190° C.; mass spectrum m/e (relative intensity) M⁻, 384 8.8), 340 (3.4), 312 (33.2), 297 (57.0), 269 (71.1), 251 (47.1), 240 (14.9), 221 (33.6), 212 (7.1), 206 (10.1), 178 (100), 150 (10.6), 121 (14.3), 91 (51.5); ¹H-NMR (d₆-Me₂SO) delta 1.23 (3H, t, J=7.1 Hz), 4.26 (2H, q, J=7.1 Hz), 4.58 (2H, s), 7.08 (1H, dt, J=2.5, 8.9 Hz), 7.32 (5H, m), 7.53 (1H, dd, J=5.8, 8.6 Hz), 7.94 (1H, dd, J=2.6, 10.7 Hz), 7.99 (1H, br s), 8.07 (1H, br s). Anal. calcd for C₂₀H₁₇FN₂O₅ (384.19): C, 62.52; H, 4.42; N, 7.29. Found: C, 62.59; H, 4.41; N, 6.98.

(R=—COO(CH₂)₅CH₃)—Method A: yield 31% after recrystallization from 2-propanol; mp 144°-145° C.; mass spectrum m/e (relative intensity) M⁻, 440 (<1), 397 (0.6), 378 (<1), 353 (<1), 312 (18.1), 294 (1.9), 269 (69.7), 251 (16.7), 240 (4.3), 221 (16.4), 212 (2.1), 194 (2.0), 178 (100), 164 (0.9), 149 (5.7), 121 (9.2), 103 (1.1), 91 (29.2); ¹H-NMR (d₆-Me₂SO) delta 0.85 (3H, br t, J=6.6 Hz), 1.24 (6H, m), 1.58 (2H, m), 4.21 (2H, t, J=6.4 Hz), 4.59 (2H, s), 7.06 (1H, dt, J=2.5, 9.0 Hz), 7.31 (5H, m), 7.54 (1H, dd, J=5.8, 8.6 Hz), 7.96 (1H, dd, J=2.5, 10.6 Hz), 8.00 (1H, br s), 8.07 (1H, br s). Anal. calcd for C₂₄H₂₅FN₂O₅ (440.24): C, 65.44; H, 5.72; N, 6.36. Found: C, 65.31; H, 5.62; N, 6.38.

We claim:
1. A compound of the formula

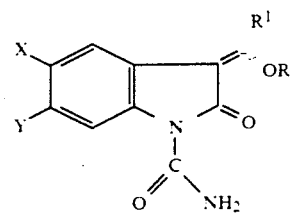

wherein X and Y are each selected from the group consisting of hydrogen, fluoro and chloro; R¹ is selected from the group consisting of 2-thienyl and benzyl; and R is selected from the group consisting of alkanoyl having two to ten carbon atoms, cycloalkylcarbonyl having five to seven carbon atoms, phenylalkanoyl having seven to ten carbon atoms, chlorobenzoyl, methoxybenzoyl, thenoyl, omega-alkoxycarbonylalkanoyl said alkoxy having one to three carbon atoms and said alkanoyl having three to five carbon atoms, alkoxycarbonyl having two to ten carbon atoms, phenoxycarbonyl, 1-(acyloxy)alkyl said acyl having two to four carbon atoms and said alkyl having one to four carbon atoms, 1-(alkoxycarbonyloxy)alkyl said alkoxy having two to five carbon atoms and said alkyl having one to four carbon atoms, alkylsulfonyl having one to three carbon atoms, methylphenylsulfonyl and dialkylphosphonate said alkyl each having from one to three carbon atoms.

2. A compound of claim 1, wherein R¹ is 2-thienyl, X is chloro and Y is hydrogen.

3. A compound of claim 2, wherein R is alkanoyl having two to ten carbon atoms.

4. The compound of claim 3, wherein R is acetyl.

5. The compound of claim 3, wherein R is propionyl.

6. The compound of claim 3, wherein R is isobutyryl.

7. A compound of claim 2, wherein R is phenylalkanoyl having seven to ten carbon atoms.

8. The compound of claim 7, wherein R is phenylacetyl.

9. A compound of claim 2, wherein R is omega-alkoxycarbonylalkanoyl said alkoxy having one to three carbon atoms and said alkanoyl having three to five carbon atoms.

10. The compound of claim 9, wherein R is omega-ethoxycarbonylpropionyl.

11. A compound of claim 2, wherein R is alkoxycarbonyl having two to ten carbon atoms.

12. The compound of claim 11, wherein R is methoxycarbonyl.

13. The compound of claim 11, wherein R is ethoxycarbonyl.

14. The compound of claim 11, wherein R is n-hexoxycarbonyl.

15. A compound of claim 2, wherein R is 1-(alkoxycarbonyloxy)alkyl said alkoxy having two to five carbon atoms and said alkyl having one to four carbon atoms.

16. The compound of claim 15, wherein R is 1-(ethoxycarbonyloxy)ethyl.

17. A compound of claim 2, wherein R is alkylsulfonyl having one to three carbon atoms.

18. The compound of claim 17, wherein R is methylsulfonyl.

19. A compound of claim 1, wherein $R^1$ is 2-thienyl, X is fluoro and Y is chloro.

20. A compound of claim 19, wherein R is alkanoyl having two to ten carbon atoms.

21. A compound of claim 20, wherein R is acetyl.

22. The compound of claim 20, wherein R is propionyl.

23. The compound of claim 20, wherein R is isobutyryl.

24. A compound of claim 19, wherein R is alkoxycarbonyl having two to ten carbon atoms.

25. The compound of claim 24, wherein R is methoxycarbonyl.

26. The compound of claim 24, wherein R is ethoxycarbonyl.

27. The compound of claim 24, wherein R is n-hexoxycarbonyl.

28. A compound of claim 1, wherein $R^1$ is benzyl, X is hydrogen and Y is fluoro.

29. A compound of claim 28, wherein R is alkanoyl having two to ten carbon atoms.

30. The compound of claim 29, wherein R is acetyl.

31. A compound of claim 28, wherein R is alkoxycarbonyl having two to ten carbon atoms.

32. The compound of claim 31, wherein R is methoxycarbonyl.

33. A method for treating inflammation in a mammal which comprises administering to said mammal an anti-inflammatory effective amount of a compound selected from claim 1.

* * * * *